US00PP25231P2

(12) United States Plant Patent
van den Top

(10) Patent No.: US PP25,231 P2
(45) Date of Patent: Jan. 13, 2015

(54) ***HOSTA* PLANT NAMED 'BRIGHT STAR'**

(50) Latin Name: ***Hosta* hybrid**
Varietal Denomination: Bright Star

(71) Applicant: Hendrik Jan van den Top, Barneveld (NL)

(72) Inventor: Hendrik Jan van den Top, Barneveld (NL)

( * ) Notice: Subject to any disclaimer, the term of this patent is extended or adjusted under 35 U.S.C. 154(b) by 113 days.

(21) Appl. No.: 13/815,273

(22) Filed: Feb. 15, 2013

(51) Int. Cl.
*A01H 5/00* (2006.01)

(52) U.S. Cl.
USPC ..... Plt./353

(58) Field of Classification Search
USPC ..... Plt./353
See application file for complete search history.

*Primary Examiner* — Susan McCormick Ewoldt
(74) *Attorney, Agent, or Firm* — C. A. Whealy

(57) ABSTRACT

A new and distinct cultivar of *Hosta* plant named 'Bright Star', characterized by its upright to outwardly spreading foliage with upright flower scapes; thick, dark green and white variegated leaves; light purple-colored flowers that are positioned above the foliar plane on strong scapes; and good garden performance.

2 Drawing Sheets

Botanical designation: *Hosta* hybrid.
Cultivar denomination: 'BRIGHT STAR'.

BACKGROUND OF THE INVENTION

The present invention relates to a new and distinct cultivar of *Hosta* plant, botanically known as *Hosta* hybrid and hereinafter referred to by the name 'Bright Star'.

The new *Hosta* plant is a naturally-occurring whole plant mutation of the *Hosta* hybrid 'Dark Star', not patented. The new *Hosta* plant was discovered and selected by the Inventor in a controlled outdoor nursery environment in Barneveld, The Netherlands during the summer of 2006.

Asexual reproduction of the new *Hosta* plant by divisions in a controlled outdoor nursery environment in Barneveld, The Netherlands since the spring of 2008 has shown that the unique features of this new *Hosta* plant are stable and reproduced true to type in successive generations.

SUMMARY OF THE INVENTION

Plants of the new *Hosta* have not been observed under all possible environmental conditions and cultural practices. The phenotype may vary somewhat with variations in environmental conditions such as temperature and light intensity without, however, any variance in genotype.

The following traits have been repeatedly observed and are determined to be the unique characteristics of 'Bright Star'. These characteristics in combination distinguish 'Bright Star' as a new and distinct *Hosta* plant:

1. Upright to outwardly spreading foliage with upright flower scapes.
2. Thick, dark green and white variegated leaves.
3. Light purple-colored flowers that are positioned above the foliar plane on strong scapes.
4. Good garden performance.

Plants of the new *Hosta* differ primarily from plants of the parent, 'Dark Star', primarily in leaf color as plants of 'Dark Star' have leaves with much narrower white-colored edges. In addition, plants of the new *Hosta* have thicker leaves than plants of 'Dark Star'.

Plants of the new *Hosta* can be compared to plants of 'Great Escape', disclosed in U.S. Plant Pat. No. 19,003. Plants of the new *Hosta* and 'Great Escape' differ primarily in the following characteristics:

1. Plants of the new *Hosta* are more upright than and not as broadly spreading as plants of 'Great Escape'.
2. Leaves of plants of the new *Hosta* are more undulate than leaves of plants of 'Great Escape'.

BRIEF DESCRIPTION OF THE PHOTOGRAPHS

The accompanying colored photographs illustrate the overall appearance of the new *Hosta* plant showing the colors as true as it is reasonably possible to obtain in colored reproductions of this type. Colors in the photographs may differ slightly from the color values cited in the detailed botanical description which accurately describe the colors of the new *Hosta* plant.

The photograph on the first sheet comprises a top perspective view of a typical flowering plant of 'Bright Star' grown in a container.

The photograph on the second sheet is a close-up view of a typical inflorescence and leaves of 'Bright Star'.

DETAILED BOTANICAL DESCRIPTION

The aforementioned photographs and following observations, measurements and values describe plants grown during the summer in 17-cm containers in an outdoor nursery in Barneveld, The Netherlands and under cultural practices typical of commercial production. During the production of the plants, day temperatures ranged from 16° C. to 28° C. and night temperatures ranged from 8° C. to 18° C. Plants were 16 months old when the photographs and description were taken. In the following description, color references are made to The Royal Horticultural Society Colour Chart, 2007 Edition, except where general terms of ordinary dictionary significance are used.

Botanical classification: *Hosta* hybrid 'Bright Star'.

Parentage: Naturally-occurring whole plant mutation of the *Hosta* hybrid 'Dark Star', not patented.

Propagation:

*Type*.—By divisions.

*Root description*.—Medium in thickness, fibrous; creamy white in color.

*Rooting habit*.—Moderate branching; medium density.

Plant description:

*Plant form and growth habit*.—Herbaceous flowering perennial plant; mounded plant form with upright to outwardly spreading foliage and upright flower scapes; flowering stems and leaves basal; low vigor to moderately vigorous growth habit; light purple-colored flowers that are positioned above the foliar plane on strong scapes.

*Plant height* (*soil level to top of foliar plane*).—About 15.7 cm.

*Plant height* (*soil level to top of inflorescences*).—About 38.4 cm.

*Plant width* (*spread*).—About 34.3 cm.

Foliage description:

*Arrangement and appearance*.—Leaves arranged in a basal rosette; leaves simple and generally symmetrical; relatively thick.

*Leaf length*.—About 11.9 cm.

*Leaf width*.—About 4.6 cm.

*Shape*.—Narrowly ovate.

*Apex*.—Long apiculate.

*Base*.—Attenuate.

*Margin*.—Entire; undulate.

*Texture, upper and lower surfaces*.—Smooth, glabrous; moderately rugose.

*Venation pattern*.—Camptodrome.

*Color*.—Developing leaves, upper surface: Center, close to 137B, 138A and 138C; towards the margins, close to 154C. Developing leaves, lower surface: Center, close to 191A; towards the margins, close to 154D. Fully expanded leaves, upper surface: Center, close to 137B and 191A; towards the margins, close to 155D; venation, similar to lamina colors, that is, close to 137B, 191A and 155D. Fully expanded leaves, lower surface: Center, close to 137C and 191A; towards the margins, close to 155D; venation, similar to lamina colors, that is, close to 137C, 191A and 155D.

*Petioles*.—Length: About 10 cm. Width: About 6 mm. Height: About 4 mm. Texture, upper and lower surfaces: Smooth, glabrous. Color, upper and lower surfaces: Center, close to 137B and 143A; towards the margins, close to 156D.

Flower description:

*Flower type and flowering habit*.—Single campanulate flowers with fused perianth arranged on terminal racemes; flowers face mostly outwardly to slightly drooping; panicles narrowly conical in shape; freely flowering habit with about 15 flowers per raceme.

*Fragrance*.—None detected.

*Natural flowering season*.—Flowering continuous from June into August in The Netherlands.

*Postproduction longevity*.—Flowers last about five days the plant; flowers not persistent.

*Flower buds*.—Height: About 2.4 cm. Diameter: About 7.5 mm. Shape: Oblanceolate. Color: Close to N82D; stripes, close to N82B.

*Inflorescence height*.—About 38.4 cm.

*Inflorescence diameter*.—About 8.2 cm.

*Flower diameter*.—About 1.5 cm.

*Flower depth*.—About 4.8 cm.

*Perianth*.—Arrangement: Three interior tepals arranged in a single whorl surrounded by an outer whorl of three exterior tepals; lower 55% of tepals fused; upper 45% of tepals flaring into a trumpet shape. Tepal length: About 5.4 cm. Tepal width: About 7 mm. Tepal lobe shape: Oblanceolate. Tepal apex: Acute. Tepal margin: Entire. Tepal texture, upper and lower surfaces: Smooth, glabrous. Tepal color: Developing and fully expanded tepals, upper surface: Close to 76C; towards the apex, close to 76A. Developing and fully expanded tepals, lower surface: Close to N82D; longitudinal stripes, close to N82C.

*Flower bracts*.—Quantity per flower: One, positioned at the base of the pedicel. Length: About 1 cm. Width: About 3 mm. Shape: Narrowly ovate; concave. Apex: Narrowly acute. Base: Cuneate. Margin: Entire. Texture, upper and lower surfaces: Smooth, glabrous. Color, upper and lower surfaces: Close to N82C.

*Peduncles* (*scapes*).—Length: About 38.1 cm. Diameter: About 2.5 mm. Aspect: Erect. Strength: Strong. Texture: Smooth, glabrous. Color: Close to 148B.

*Pedicels*.—Length: About 7 mm. Diameter: About 1 mm. Aspect: About 50° from peduncle axis. Strength: Strong. Texture: Smooth, glabrous. Color: Close to 76B.

*Reproductive organs*.—Stamens: Quantity per flower: Typically six. Filament length: About 5 cm. Filament color: Close to 145D. Anther shape: Narrowly oblong; dorsifixed. Anther length: About 5 mm. Anther color: Close to 200B. Pollen amount: Scarce to moderate. Pollen color: Close to 15A.

*Pistils*.—Quantity per flower: One. Pistil length: About 5.5 cm. Style length: About 5.3 cm. Style color: Close to 155D. Stigma shape: Crested. Stigma color: Close to 155C. Ovary color: Close to 150C.

*Seeds and fruits*.—Seed and fruit development have not been observed on plants of the new *Hosta*.

Disease & pest resistance: Plants of the new *Hosta* have not been noted to be resistant to pathogens and pests common to *Hosta* plants.

Garden performance: Plants of the new *Hosta* have been observed to have good garden performance and to tolerate rain, wind and high temperatures about 32° C., and to be hardy to USDA Hardiness Zone 5.

It is claimed:

1. A new and distinct *Hosta* plant named 'Bright Star' as illustrated and described.

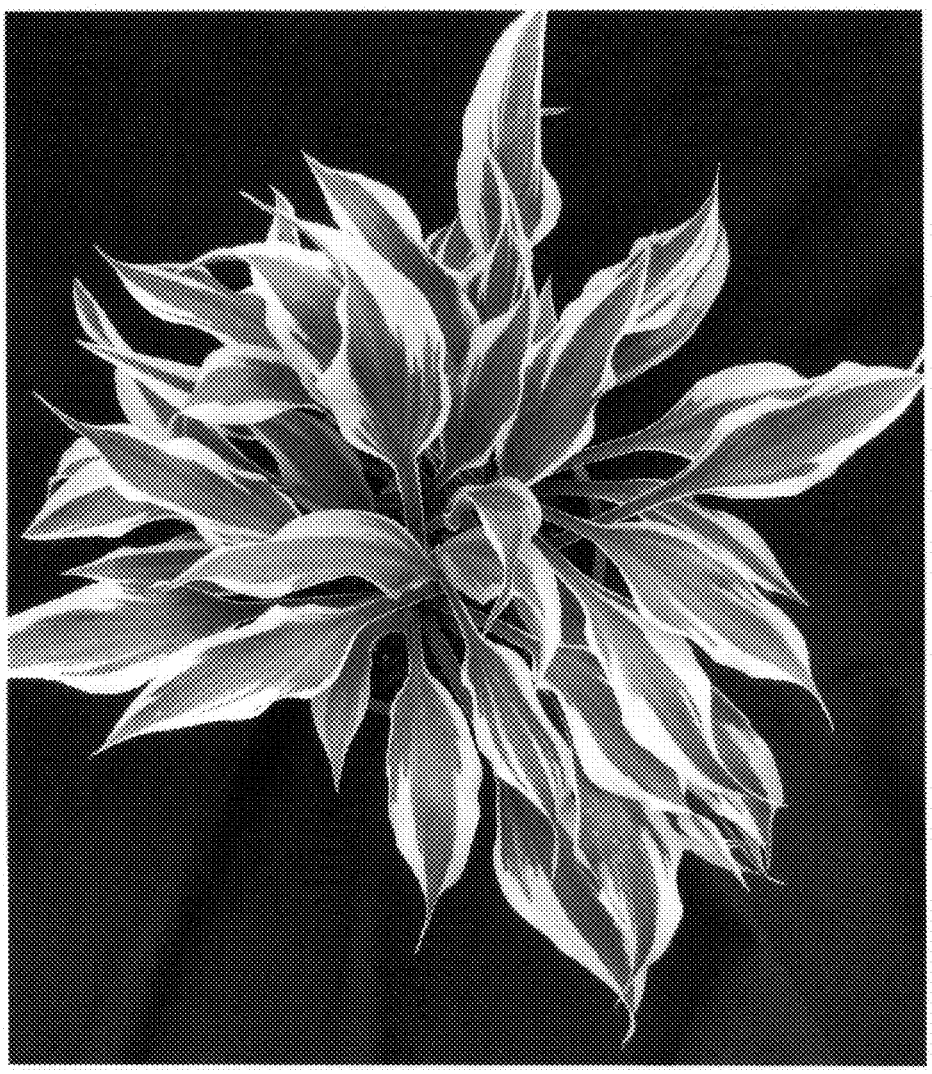

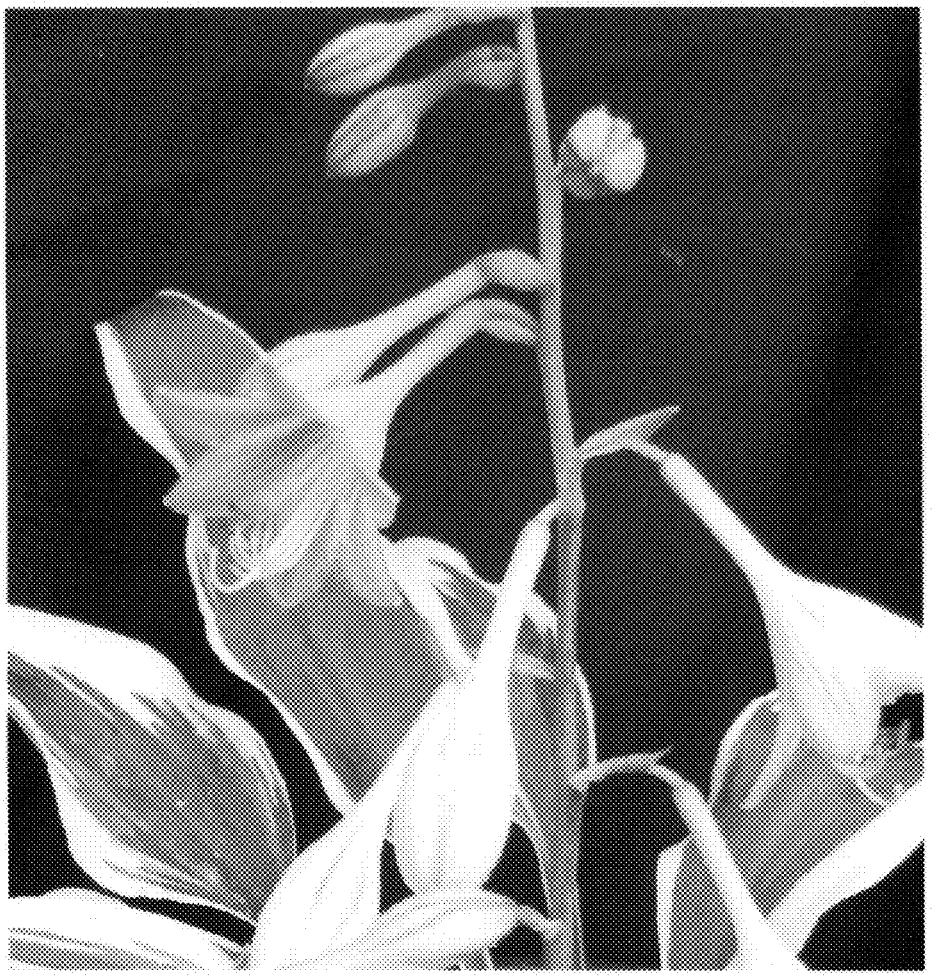

* * * * *